United States Patent [19]

Tam

[11] Patent Number: 5,483,080

[45] Date of Patent: Jan. 9, 1996

[54] METHOD AND DEVICE FOR MEASURING AND CONTROLLING CELL DENSITY IN MICROBIOLOGICAL CULTURE

[76] Inventor: Lisa A. Tam, 3618 Vermont St., Long Beach, Calif. 90814

[21] Appl. No.: 281,523

[22] Filed: Jul. 26, 1994

Related U.S. Application Data

[63] Continuation of Ser. No. 947,045, Sep. 18, 1992, abandoned.

[51] Int. Cl.$^6$ .................................................. G01N 15/06
[52] U.S. Cl. ........................................... 250/574; 356/338
[58] Field of Search ................................... 250/574, 575, 250/222.2; 356/338, 336, 342, 442, 326, 343

[56] References Cited

U.S. PATENT DOCUMENTS

| | | | |
|---|---|---|---|
| 3,319,514 | 5/1967 | McAllister, Jr. | 356/442 |
| 3,714,444 | 1/1973 | Carr et al. | 356/442 |
| 4,447,150 | 5/1984 | Heinemann . | |
| 4,740,709 | 4/1988 | Leighton . | |
| 5,007,740 | 4/1991 | Jeannotte . | |
| 5,114,860 | 5/1992 | Hayashi | 356/338 |
| 5,175,438 | 12/1992 | Ikeda | 250/574 |

OTHER PUBLICATIONS

Jeffrey A. Titus, Gregory W. Luli, Michael L. Dekleva, William R. Strohl, Application Of A Microcomputer–Based System To Control And Monitor Bacterial Growth, Applied and Environmental Microbiology, vol. 47, No. 2, Feb. 1984, pp. 239–244.

M. Ohashi, T. Watanabe, T. Ishikawa, and Y. Watanabe, Sensors And Instrumentation: Steam–Sterilizable Dissolved Oxygen Sensor And Cell Mass Sensor For On–Line Fermentation System Control, Biotechnology and Bioengineering Symp. No. 9, 105–116 (1979).

Dane W. Zabriskie, Use Of Culture Fluorescence For Monitoring Of Fermentation Systems, Biotechnology and Bioengineering Symp., No. 9, pp. 117–123 (1979).

B. W. Shimmons, W. Y. Svrcek and J. E. Zajic, Cell Concentration Control By Viscosity, Biotechnology and Bioengineering, vol. XVIII, pp. 1793–1805 (1976).

K. Sakato, H. Tanaka, M. Samejima, Electrochemical Measurements Of Cell Populations, Research Laboratory of Resources Utilization, Tokyo Institute of Technology, Yokohama 227, Japan, pp. 321–334, 1981.

Dane W. Zabriskie and Arthur E. Humphrey, Real–Time Estimation Of Aerobic Batch Fermentation Biomass Concentration By Component Balancing, AIChE Journal, vol. 24, No. 1, Jan., 1978, pp. 138–146.

John C. Fieschko, Fermentation Technology Using Recombinant Microorganisms, Biotechnology, vol. 76, 1989, pp. 118–138.

Mehmet A. Gencer, Determiantion Of Biomass Concentration By Capacitance Measurement, Biotechnology and Bioengineering, vol. XXI, pp. 1097–1103 (1979).

Primary Examiner—David C. Nelms
Assistant Examiner—Que T. Le
Attorney, Agent, or Firm—Stetina Brunda & Buyan

[57] ABSTRACT

A method and device for measuring the concentration of solids within a liquid medium, or other optical properties of a liquid solution or suspension, by the technology of reflectance. In a preferred embodiment, the reflectivity measuring device of the present invention comprises a measuring head or probe having at least one radiation source and at least one radiation sensor positioned therein. The head or probe is attached to a controller/data readout having a microprocessor control system housed therein. The head or probe is positioned within or adjacent a body of liquid. Thereafter, the radiation source is caused to emit radiation and the radiation sensor is utilized to sense the relative amounts of radiation reflected by the body of liquid and/or solids contained therein. The invention is applicable to any system wherein it is desirable to measure solids content or optical properties of liquids, including biological culture systems wherein it is desirable to measure the density or population of microorganisms cells within a liquid culture medium.

27 Claims, 7 Drawing Sheets

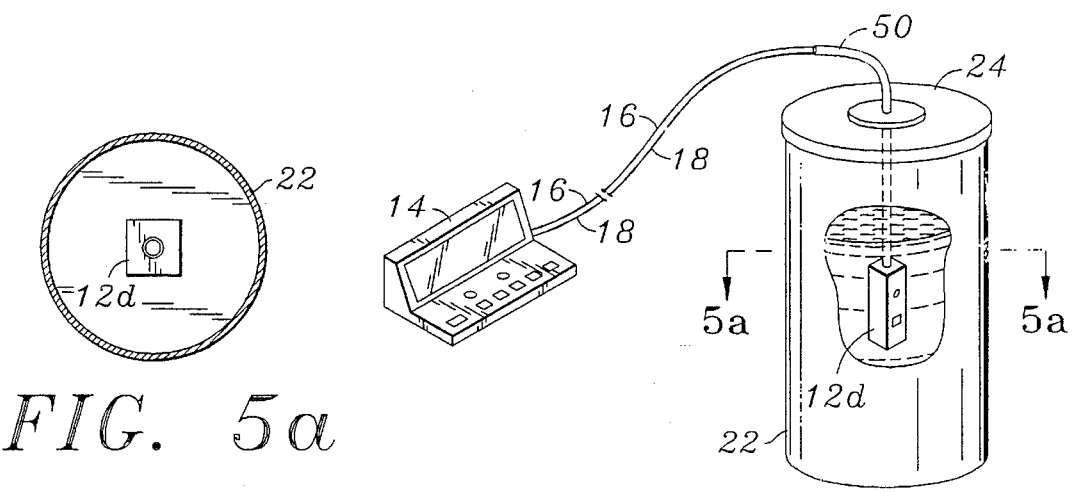
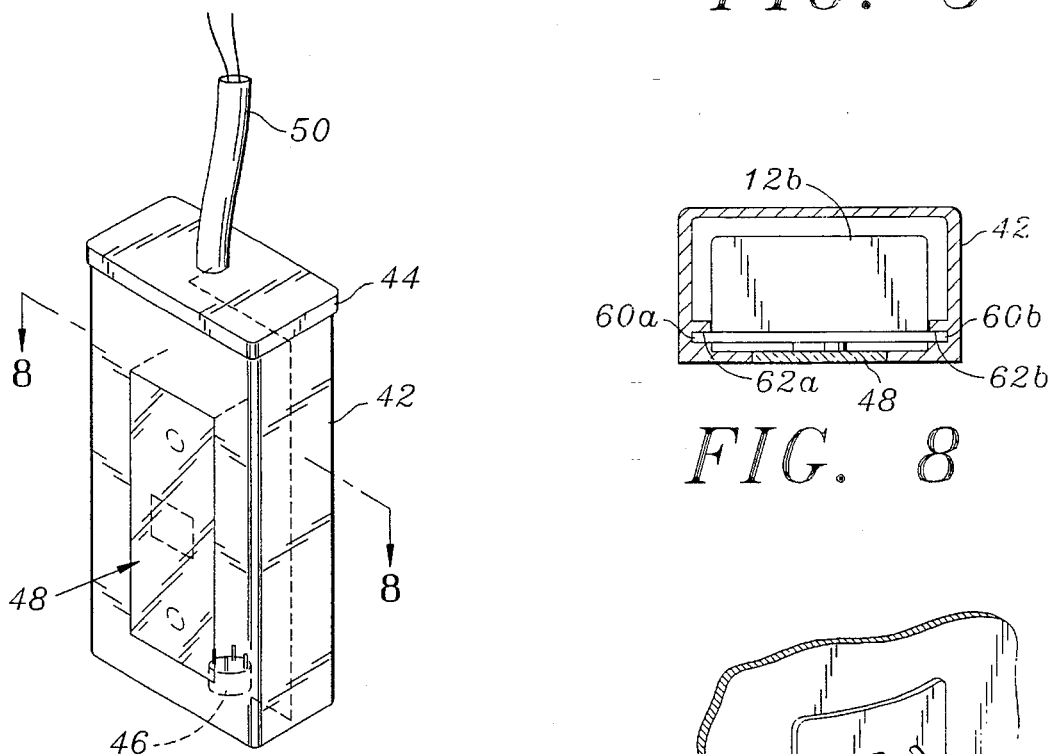
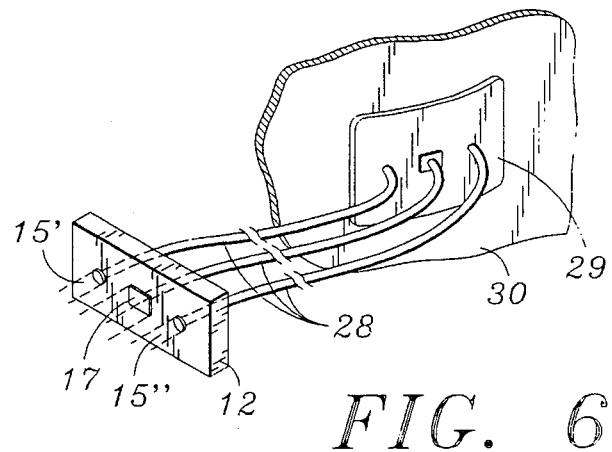

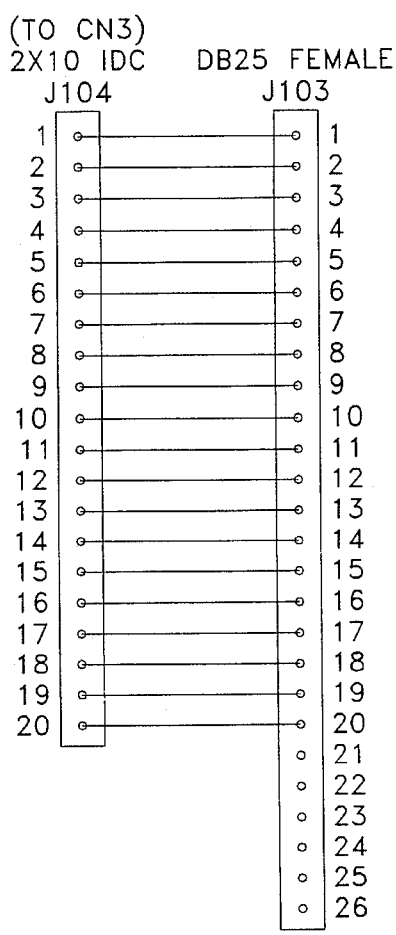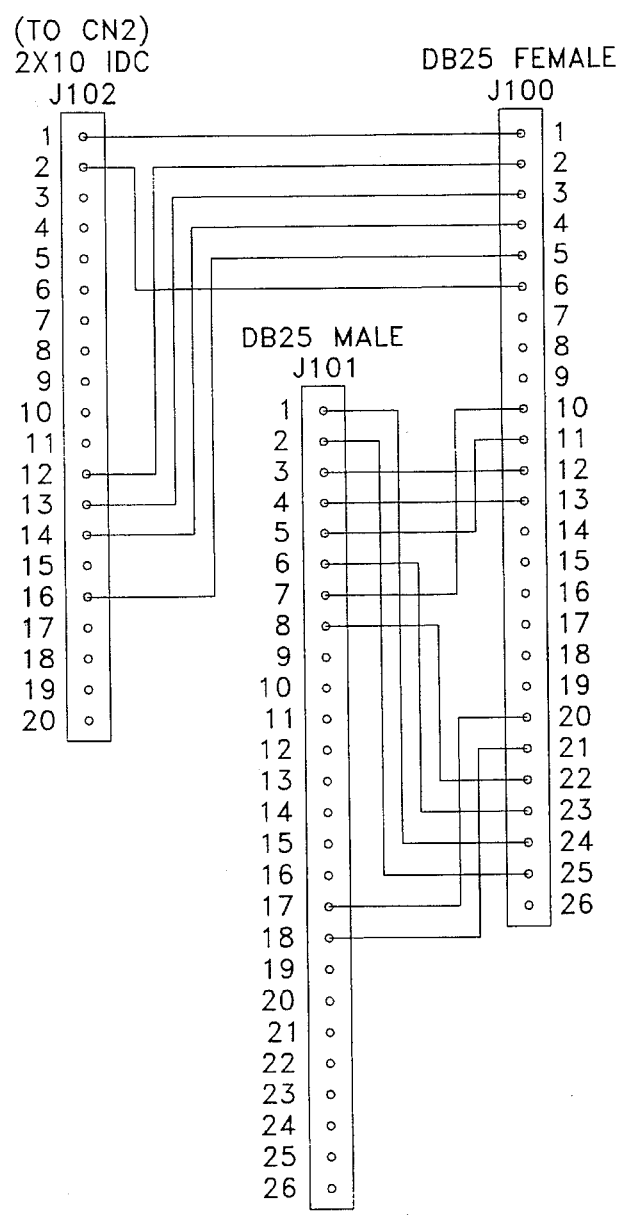
*FIG. 11*

METHOD AND DEVICE FOR MEASURING AND CONTROLLING CELL DENSITY IN MICROBIOLOGICAL CULTURE

This is a continuation of application Ser. No. 07/947,045, filed on Sep. 18, 1992, now abandoned.

FIELD OF THE INVENTION

The present invention relates generally to methods and devices for determining and/or analyzing properties of suspensions and solutions, and more particularly to a method and device for determining and analyzing reflectometric properties of solutions or suspensions such as the density or concentration of solid matter in a liquid medium. (e.g. cell density in a liquid biological culture medium)

BACKGROUND OF THE INVENTION i. Methods and Devices for Measuring the Density of Solids Suspended in Liquid Media Many industrial and laboratory processes require the periodic or continual measurement of the density of solid matter suspended within a liquid matrix. Such measurements are particularly commonplace in the biotechnology, water treatment, petroleum, chemical, pharmaceutical and food processing industries.

One type of instrument which has heretofore been utilized to measure the density of solid particles suspended in a liquid medium is the optical densitometer or spectrophotometer.

A spectrophotometer instrument typically comprises a light source positioned in a first location and a sensor positioned at a second location, such that light from the light source must pass through the liquid medium wherein the solid particles are suspended prior to reaching the sensor. The density of the solid particles within the liquid medium is then determined based on the relative amount of light energy transmitted from the light source to the sensor.

The existence of gas bubbles, voids or solid clusters within the liquid medium may interfere with the measurement of solids concentration by standard spectrophotometer techniques, as such gas bubbles or voids may prevent or disrupt transmission of light energy through the liquid medium.

The existence of such gas bubbles, voids or solid clusters is commonplace in systems wherein the liquid medium is under constant agitation, circulation or aeration. Accordingly, there exists a need in the art for improved methods and devices for measuring the density of suspended solids within liquid media wherein there exists numerous gas bubbles, voids or clusters such as those created by circulation, agitation or aeration of the liquid medium.

ii. Methods and Devices for Measuring Cell Density in Microbiological Cultures In many laboratory and industrial applications it is desirable to obtain accurate and reproducible measurements of the concentration or density of microorganisms—or biological cells being grown in a liquid broth or culture medium. Such measurements of cell density are critical to the proper control of variables which influence cell growth rate (e.g., temperature, pH, agitation, dissolved oxygen, nutrient levels, etc. . . . ).

Modern advancements in the science of recombinant gene technology have given rise to new possibilities for large scale production of difficult-to-synthesize chemical substances, through the controlled fermentation or culture of genetically recombinant microorganisms, as well as "wild type" microorganisms. The industrial fermentation or culture of genetically recombinant microorganisms is typically effected by growing the recombinant microorganisms under aseptic conditions within a liquid growth medium contained in a bioreactor or fermentation vessel. Such bioreactor or fermentation vessels generally comprise an enclosed vessel outfitted for precise microprocessor or computer effected control of variables such as nutrient feed rate, temperature, pH and aeration/dissolved oxygen content. Periodic or continuous measurements of cell density are utilized as a basis for making corresponding changes in process variables (e.g. temperature, pH, agitation, aeration, dissolved oxygen, nutrient feed rate, etc. . . . ). Thus, it is highly desirable to obtain continuous or periodic measurements of cell density, especially of high cell density, which are accurate and which are substantially free of noise, or artifactual readings caused by the presence of entrained gas bubbles, voids or solid clusters within the liquid culture medium.

It is difficult to obtain accurate measurements of cell density using optical density measuring instruments in systems wherein the concentration of cellular matter or solids in the liquid culture medium is very high or excessive. In such applications, the high cell density or solids concentration may impair or inhibit optical transmittance through the medium to such a degree as to render the desired optical density measurement unobtainable or unreliable. Optical density is typically linear only for low cell densities (e.g., up to 0.5 g/l of *Saccharomyces cerevisiae*).

Thus, there remains a need in the art for improved methods and instruments for obtaining continuous or periodic measurements of cell density in liquid culture media wherein the cell concentration is extremely high and/or wherein changes in process variables are occurring.

SUMMARY OF THE INVENTION

The present invention provides a reflectance measuring instrument and device for measuring reflectometric properties of solutions and suspensions. The present invention finds particular utility in measuring the concentration or density of solids (e.g., cellular matter) suspended within a liquid medium (e.g., a biological culture medium) or other reflectance-determining properties (e.g., depth of color) of solutions or suspensions.

In accordance with the invention, there is provided a method for measuring the reflectance of a sample solution or suspension, said method comprising the steps of:

a.) positioning at least one radiation source so as to cast radiation into said sample;

b.) positioning at least one radiation sensor adjacent said at least one radiation source to receive reflected radiation which has emanated from said at least one radiation source and reflected from said sample; and c.) determining the reflectance of said sample by determining the difference between the amount of radiation cast into said sample by said at least one radiation source and the amount of reflected radiation received by said at least one radiation sensor.

Further in accordance with the invention, there is provided a device for measuring the reflectometric properties of solutions or suspensions, said device comprising:

a.) at least one radiation emitting means positioned at a first location on said device;

b.) at least one radiation sensing means positioned at a second location on said device;

c.) said at least one radiation emitting means and said at least one radiation sensing means being positioned and spaced relative to one another on said device such that when said device is positioned next to a sample body of liquid radiation emitted by said emitting means will pass into said body of liquid such that a portion of said radiation will be reflected from said body of liquid and further such that reflected radiation reflecting from said body of liquid will be sensed by said at least one radiation sensor; and d.) means for determining the difference between the amount of radiation emitted by said at least one emitter means and the amount of radiation sensed by said at least one sensing means.

Still further in accordance with the invention, the methods and devices of the present invention may be operated such that radiant energy emitted by the radiation source(s) is in the wavelength range of 300 nm–1050 nm. The radiation sensor(s) of the device may be specifically adapted to sense only radiation within the wavelength range being emitted by the radiation source(s) of the device and not other wavelengths outside the range emitted by the device.

Still further in accordance with the invention, a control and monitoring console or component may be connected to the reflectance measuring device of the present invention to provide means for programming controlling the output and operation of the device and/or to provide means for calibrating, reading and recording data obtained through operation of the device.

Further objects and advantages of the invention will become apparent to those skilled in the art upon reading and understanding of the following detailed description and the accompanying drawings.

BRIEF DESCRIPTION OF THE DRAWINGS

FIG. 5 is a perspective view of an instrument of the present invention wherein the measuring head component of the device is fully submersed within a liquid medium.

FIG. 5a is a cross-sectional view through line 5—5 of FIG. 5.

FIG. 6 is a perspective view of a flexible optical fiber connector apparatus for connecting an instrument of the present invention to a vessel, such as a tank or fermenter, wherein a liquid medium is contained.

FIG. 7 is a perspective view of a submersible liquid-tight enclosure or encapsulation unit, having the measuring head component of an instrument of the present invention operatively mounted therein.

FIG. 8 is a cross-sectional view through line 8—8 of FIG. 7.

FIG. 11 is a schematic electrical diagram of the cabling of an instrument of the present invention.

DETAILED DESCRIPTION OF THE PREFERRED EMBODIMENT

Figure 1:
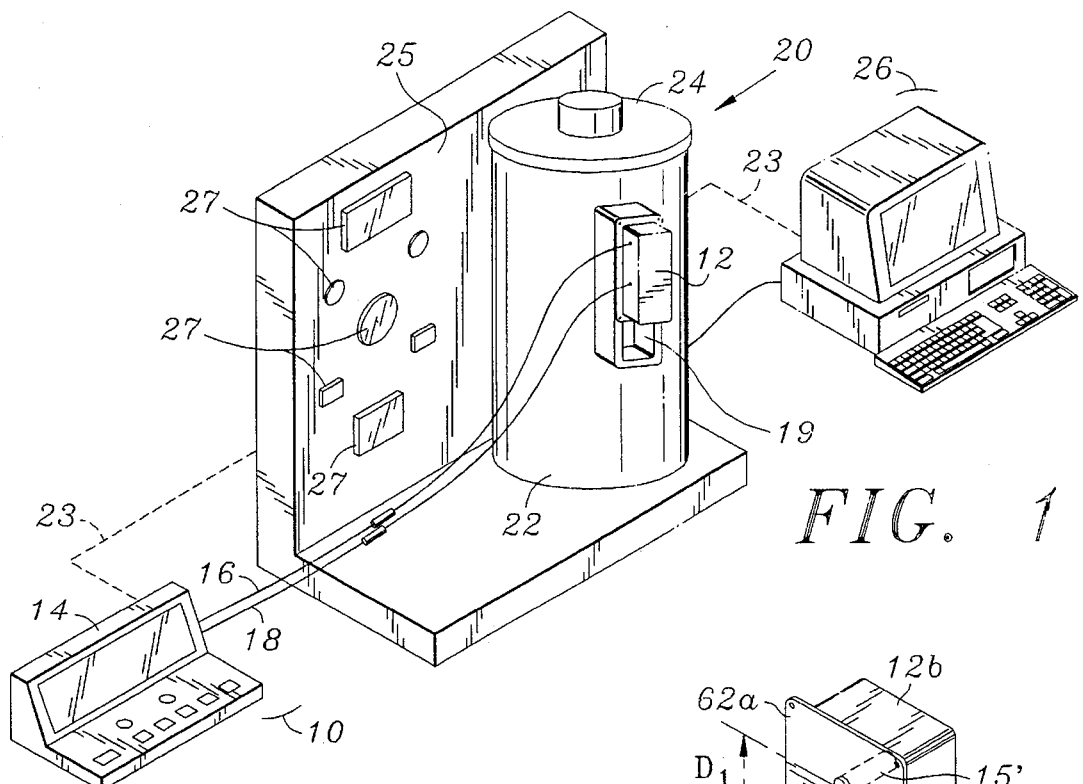
FIG. 1 is a perspective view of a reflectance measuring instrument of the present invention operatively mounted on a typical bench top biological fermentation system.

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments and may be satisfactorily applied for the measurement of any suspension or solution which may exhibit similar behavior that are also intended to be encompassed within the spirit and scope of the invention.

The term "reflectance" as used in this patent application, refers to the reflected radiation which results from all factors which effect the amount of radiation received and sensed by the radiation sensing component of the instrument of the present invention. As with any optical measurement, the "reflectance" measured by the instrument is influenced by a composite of many optical properties of the medium (e.g., diffuse reflectance, absorbance and transmittance).

The detailed description set forth herein will make reference to the measurement of solids concentration (e.g., cell density) suspended in a liquid medium. The method and instruments of the present invention may also find application in solutions, as opposed to suspensions, provided that such solutions exhibit a color change or other change in the index of refraction of the solution in response to concentration of one or more particular components of the solution. For example, in some solutions a color change of the liquid medium may occur based on the amount of dissolved oxygen in the solution. Also, some solutions may contain color indicators, such as indicator dyes (e.g., toluidine blue), which change color or intensity in response to the concentration of a particular component (e.g., the anticoagulant Heparin) mixed in the solution. In such applications, the instrument of the present invention may be utilized to determine changes in reflectance which occur secondary to the alterations in color or color intensity of the solution.

The method and instruments of the present invention may also be useable in the gas phase. For example, in the petroleum industry measurements of the amount or concentration of a specific component in the effluent gas of a cracking tower may be effected by application of the method(s) or instrument(s) of the present invention. Similarly, the method(s) and/or instrument(s) of the present invention may be utilized to determine the amount of gas in a liquid phase, such as the concentration of air bubbles in a liquid medium. Thus, although the hereinafter-set-forth description refers specifically to the measurement of solids suspended in a liquid medium, it will be appreciated that the method(s) and instrument(s) of the present invention are also applicable in solutions and/or gas media applications.

Referring to the drawings, a reflectance measuring instrument 10 of the present invention may be utilized to measure the concentration of microorganisms within a typical bioreactor or fermenter system 20, such as that shown in FIG. 1.

In the embodiment shown, the reflectance measuring instrument 10 of the present invention comprises a reflectance measuring probe or head 12 attached to a controller/readout component or console 14 by way of wires or lines 16, 18.

A typical bench top bioreactor or fermenter with which the reflectance measuring instrument 10 of the present invention may be utilized comprises a fermentation vessel 22 having a solid lid 24 positioned thereon, said fermentation vessel 22 being connected to various dials, gauges and switches 27 on control panel 25 by way of appropriate wires, tubes, sensors and/or other components.

A computer or microprocessor controller 26 is connected to the control panel portion 25 or vessel portion 22 of the bioreactor 20 in order to provide pre-programmed control of process variables and/or on-line data treatment, logging, analysis, graphing and/or computation.

Process variables which are typically monitored and controlled include nutrient feed rate, temperature, pH, dissolved oxygen content (DO), gas analysis, surface foaming/antifoam content and agitation rate.

Examples of commercially available bioreactors or fermenters 20 with which the reflectance measuring instrument 10 of the present invention may be utilized, include those commercially available under the names BioFlo I, BioFlo II, BioFlo III, MicroGen and Micros I (from New Brunswick Scientific Co., Inc, Box 4005, 44 Talmadge Road, Edison, N.J. 08818-4005), and Biostat MD, Biostat ED and Biostat B (from B. Braun Biotech, Inc., 999 Postal Rd., Allentown, Pa. 18103). Additionally, the reflectance measuring instruments 10 of the present invention may be utilized in connection with large bioreactor plants or fermentation plants, wherein biological cultures are maintained in industrial vessels sized to contain 75–100,000 liters or more of liquid culture medium.

The preferred embodiment of the instrument 10 incorporates at least one radiation source 15, positioned within the probe or head portion 12 of the instrument 10. The radiation source 15 is preferably operative to emit radiation within the ultraviolet to infrared range. The radiation source 15 may comprise any suitable type of lamp or radiation source including, but not limited to, lasers, light emitting diodes (LEDs), or other light sources such as incandescent lamps or gas vapor lamps equipped with filters.

A radiation sensor 17 is also positioned on or within the head or probe component 12 of the instrument 10. The radiation sensor 17 may comprise any suitable type of radiation sensor operative to receive and sense radiation from the radiation source 15 which has been reflected from one or more objects or a body of liquid (e.g. solution or suspension) and returned to the frontal face or receiving portion of the sensor 17.

Figure 2:
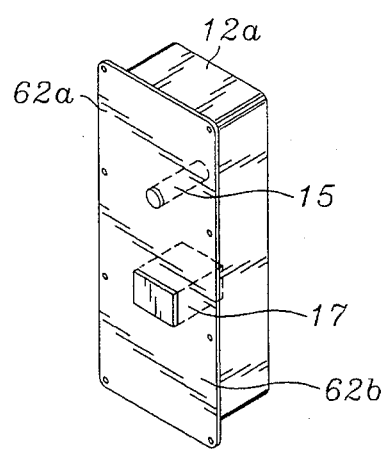
FIG. 2 is a perspective view of a first embodiment of the measuring head component of an instrument of the present invention wherein a single light emitting diode and a single sensor are mounted within a housing.
Figure 3:
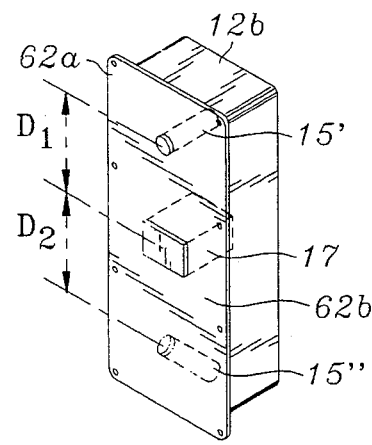
FIG. 3 is a perspective view of an alternative embodiment of the measuring head component of an instrument of the present invention wherein two (2) light emitting diodes and a single sensor are positioned within a housing.

In the embodiments shown in FIGS. 2 and 3, the radiation sensor 17 comprises a photodiode having a substantially flat band with response which encompasses the wavelength(s) of radiation emitted by the radiation source(s) 15. Examples of commercially available photodiodes which may be utilized in this instrument 10 include Model Nos. BPX65 and AX65-R2F (Centronics, Inc., 1829 DeHavilland Drive, Newbury Park, Calif. 91320) and Model Nos. PDB-V103 and PDB-C105 (Photonic Detectors, Inc., 90-A W. Cochran St., Simi Valley, Calif. 93065.

The output of the radiation source 15 may be in any wavelength range suitable for the particular application. In many applications, the radiation output of the radiation source 15 will be in the visible or infrared ranges. Light within ultraviolet ranges may also be used, but may be adversely affected in some applications by the presence of cytochromes within the liquid medium or solid matter contained therein.

The radiation source is connected to the control/read-out console 14 by way of wire or line 16. The radiation sensor 17 is connected to the control/read-out console 14 by way of wire or line 18. By such interconnections, electrical signals provided by the control/read-out console 14 will pass through line 16 to cause radiation source(s) 15 to emit the desired light or radiation. The amount of radiant energy that the radiation source(s) 15 emit is controllable by varying the electric signal emitted by the controller circuitry of the control/data console 14 or by optical or other means. Examples of "optical" means by which such control may be accomplished include the utilization of a lamp accompanied by appropriate filters and/or coatings or a polarized source, such as a laser, passed through a crystal modulator, or a liquid crystal shutter to accomplish such optical regulation. Thus, while the disclosure herein refers to radiation sources controlled by means of electrical current from the control/readout console 14, other known modes of control may also be utilized.

The output of the radiation sensor 17 may comprise or be in the form of variations in either voltage or current. The electrical output of the radiation sensor 17 passes through line 18 to the controller/data readout console 14 wherein the controller receives, amplifies and/or buffers the signal as needed. A corresponding value or graphic representation is then displayed on the screen of the control/data readout console 14.

In the installation shown in FIG. 1, the variations in current or voltage of the signal returning to the control/data readout console 14 from the radiation sensor 17 within head or probe 12 are proportional to the amount of radiation emitted from radiation source 15 and subsequently reflected to, and received by, the receiving face of radiation sensor 17. Such reflection is the result of cellular matter contained within the culture liquid with bioreactor vessel 22. The mathematical relationship between the current or voltage variations and the corresponding cell density of the culture is well understood by those skilled in the art.

Figure 4:
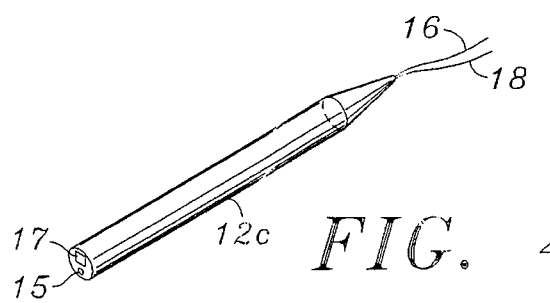
FIG. 4 is a perspective view of another alternative embodiment of the measuring head component of the device of the present invention wherein a single light emitting diode and a single sensor are positioned in an elongate cylindrical housing.

The head or probe 12 component of the device may be in the configuration of an enclosed unit such as the unit shown in FIGS. 1, 2 and 3. Alternatively, the head or probe 12 may be in the configuration of an elongate cylindrical or otherwise elongate shaped probe, such as that shown in FIG. 4. Such elongate probe 12c may be specifically sized and configured to be insertable through standard inspection ports formed in typical bioreactors and fermentation vessels existing in the art.

The radiation source(s) 15 and radiation sensor 17 of the head or probe 12 may be provided with frontal lenses or windows through which such components may freely emit and/or receive radiation. It will be appreciated that such frontal window or lens need not necessarily be "transparent" to visible light so long as it is sufficiently transparent or transmissible to the radiation (e.g., infrared) emitted by the radiation source 15 of the instrument. When such windows are submersed within or positioned adjacent a window or inspection port 19 formed in a vessel (e.g. bioreactor or fermentation vessel 22 shown in FIG. 1), the instrument 10 will be thereby rendered operative to effect periodic or continuous reflectance measurements of the contents of the vessel.

Optionally, elongate light transmitting members such as optical fibers 28 shown in FIG. 6 may be utilized to optically connect the lenses or light emitting portions of the radiation source(s) 15', 15 to a window or inspection port 29 formed in the wall of a vessel or container 30 and, likewise, the lens or receiving portion of the radiation sensor 17 to another point on the window or port 29 formed in the wall of said container 30, so as to permit the probe or head 12 component of the instrument 10 to be positioned remotely from the vessel or container and still carry out its desired reflectance measuring function.

As shown in FIG. 5, the head or probe 12d of some embodiments may be submersible in liquid so as to be lowerable directly into the liquid medium contained within a vessel 22b. In such embodiments, the probe or head 12d will preferably be provided or positioned within a liquid tight outer case which is suitable for sterilization, by gas, radiation, autoclave, or other types of sterilization/disinfection. Alternatively, a standard probe or head 12, 12a, 12b, 12c may be positioned within a liquid tight outer capsule or enclosure 42, as shown in FIGS. 7 and 8. Additionally, one or more positioning tracks, lips, members, protrusions, clips, clamps, springs or other positioning or sealing members may be formed on the interior of the capsule or enclosure 42 to position, urge or hold the probe or head 12 into operative position adjacent the window 48 of the capsule or enclosure 42. For example, in FIG. 8, the capsule or enclosure 42 is provided with elongate receiving tracks or grooves 60a, 60b on opposite sides of the interior wall thereof, adjacent the frontal window 48. Such tracks or grooves 60a, 60b are positioned and figured to slideably receive therein the lateral lips 62a, 62b of the head or probe 12a, 12b such that, when the head or probe 12b is advanced fully into said tracks 60a, 60b, the radiation source(s) 15 and radiation sensor 17 of the head or probe 12b will be positioned immediately adjacent or against window 48. The particular embodiment of the head or probe 12b shown in FIG. 7 and 8 is provided with a male plug or receiving receptacle on the bottom end thereof such that when fully operatively advanced to its operative position within capsule or enclosure 42, plug member 46 positioned in the bottom of capsule 42 will be received into the receptacle or female plug (not shown). The fixed male plug member 46 is connected by wiring within the capsule or enclosure 42 to wires within the flexible tether 50, thereby providing for operative interconnection of the probe or head 12b to the controller/data readout console 14 of the instrument 10 when the probe or head 12b is operatively positioned within the liquid tight capsule or enclosure 42 and fully submersed in a vessel or container of liquid, in the manner shown in FIG. 5. Other means of electrical connection may be appreciated by those acquainted with the art.

In other embodiments, the probe or head 12 may be formed of material which is easily sterilizable by gas, radiation, autoclave or other means. Alternatively, the probe or head 12 may be made disposable such that, after each use, the probe or head may be discarded, thereby eliminating any need for subsequent sterilization/disinfection, or connection to the vessel or container.

The preferred embodiment of the instrument 10 of the present invention includes a circuit which employs pulse multiplying and integrating techniques to provide a high intensity of light for a short period of time. The circuit employs digital technology which provides a circuit unaffected by temperature and noise. The circuit also employs microprocessor technology which allows compensation for air bubble and background light interference.

Figure 9:
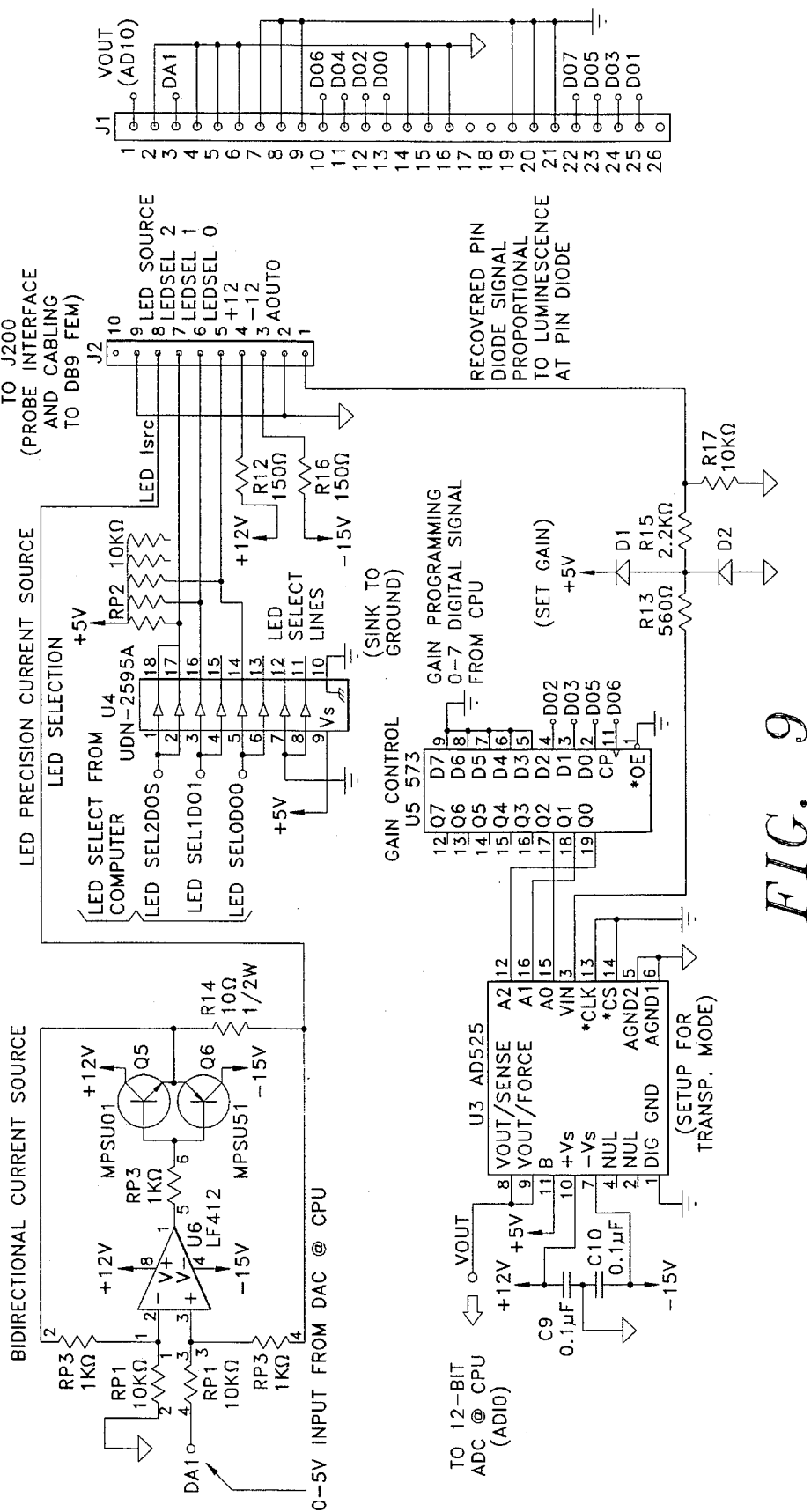
FIG. 9 is a schematic electrical diagram of the controller/data display component of a reflectance measuring instrument of the present invention.
Figure 10:
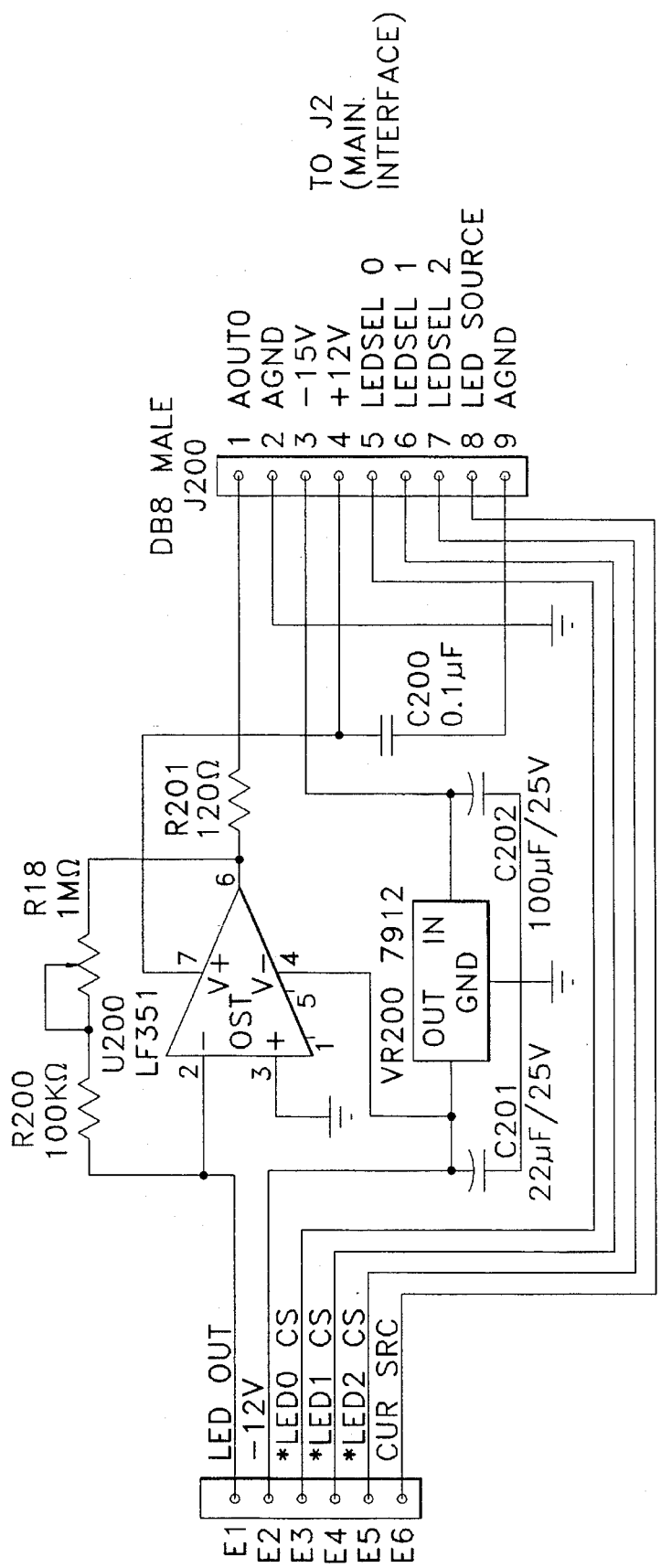
FIG. 10 is a schematic electrical diagram of the sensor head component of a reflectance measuring instrument of the present invention.

The circuitry of the preferred instrument 10 of the present invention is shown in FIGS. 9–11. Specifically, FIG. 9 is an electrical diagram of the main interface, FIG. 10 is an electrical diagram of the probe or head and FIG. 11 is a diagram of the cabling of the instrument 10.

The main interface shown in the diagram of FIG. 9 comprises circuitry which allows a computer to operate as the instrument 10. The section labeled "TO DB9 FEM" is the interface to the cabling of the head or probe 12 of the instrument 10. The top section marked "bi-directional current source" is the source that fires the radiation source(s) 15 (e.g., LEDs), the amount of light that is emitted from the radiation source(s) 15 is determined by the 0–5 volt input. The main interface shown in FIG. 9 further comprises radiation source select drivers U4. Such radiation source select drivers determine which radiation source 15 emits its radiation or light at the appropriate time(s). Additionally, the main interface shown in FIG. 9 comprises the circuitry of a programmable gain amplifier U3, which incorporates a buffer system. The output of the programmable gain amplifier U3 ultimately goes to an analog to digital converter (not shown) to output the raw data which represents values linearly related to the amount of reflected radiation sensed by the radiation sensor 17.

The circuit diagram of the probe shown in FIG. 10 includes a portion marked "DB9 MALE". This portion of the circuitry comprises the connection whereby the head or probe 12 is connected to the main interface of the instrument shown in FIG. 9. The probe circuitry includes a regulated (−12 v) power supply that sources the radiation detector. In the embodiment shown, the radiation detector, preferably comprises a photodiode.

The photodiode is forward biased for stability and sensitivity. The means by which such forward biasing of the photodiode is accomplished comprises pin E1 of the hybrid interface, held at 0 volts by transimpedance recovery amplifier U200. The anode of the photodiode is sourced by −12 volts, as previously described. Additionally, the circuitry of the head or probe, as shown in FIG. 10, may comprise a transimpedance recovery amplifier U200 such as that commercially available as LF351, LF411, or a similar amplifier with associated circuitry.

In accordance with the circuitry shown in FIGS. 9–11 filtered reflectance data is attained by subjecting the raw signal output of the radiation sensor 17 to an "if loop" and a five point moving average. There exists a disparity in the index of refraction of air as compared to that of microorganisms or cells. Such disparity in the index of refraction results in the differences in the reflection from cellular matter as opposed to the reflection from air bubbles. The difference in reflectance is large enough to be detected by the present invention allowing the utilization of a simple data filtering scheme.

Figure 13:
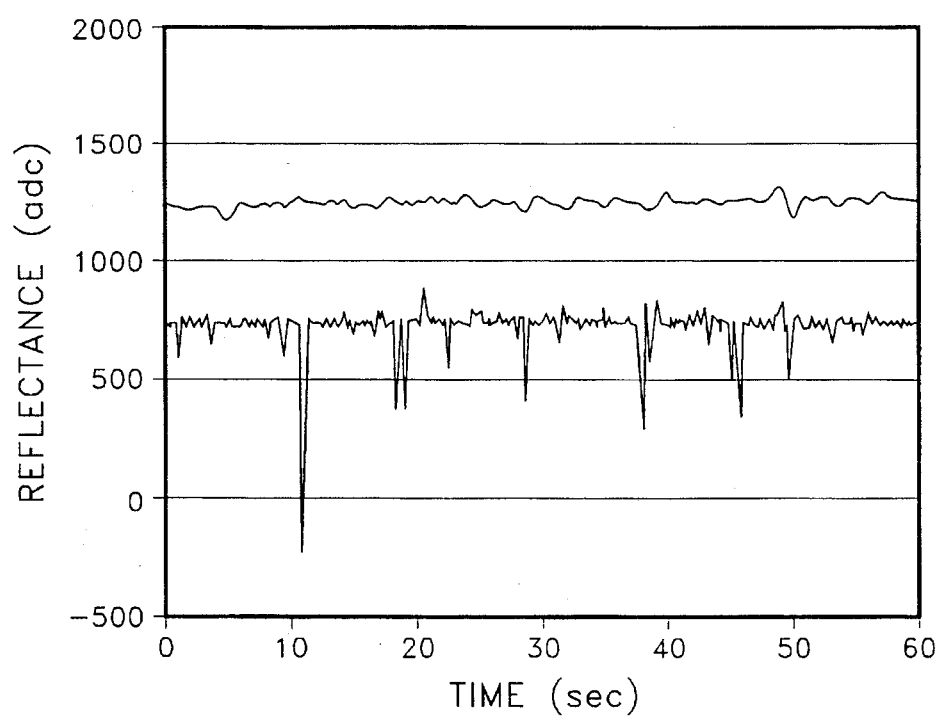
FIG. 13 is a graphic illustration showing both filtered and unfiltered data signals generated by a reflectance measuring instrument of the present invention in an air bubble containing medium.
Figure 14:
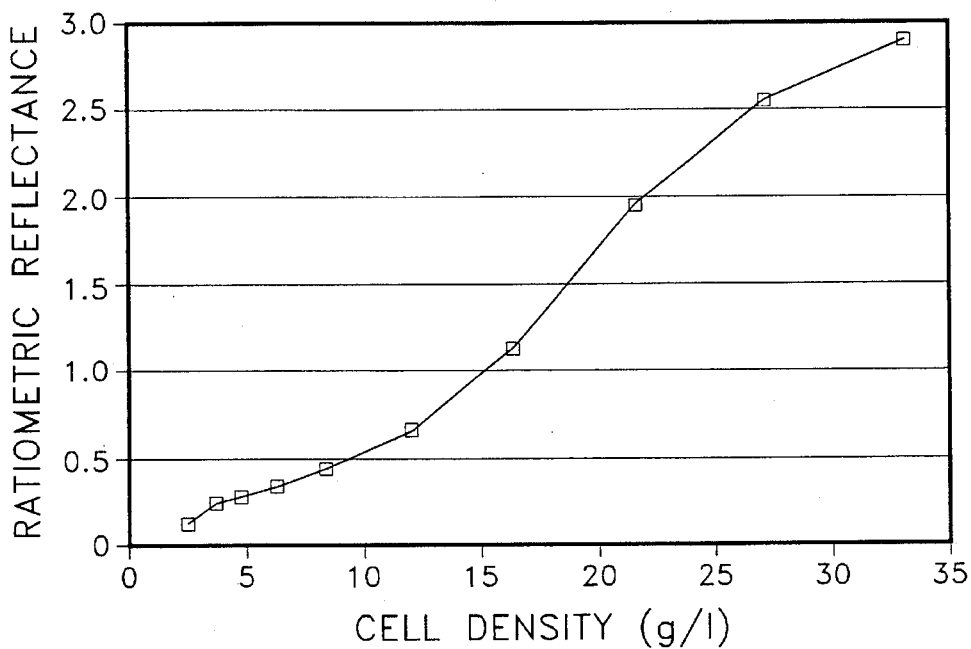
FIG. 14 is a graphic illustration showing ratiometric reflectance measured by an instrument of the present invention in samples containing varied concentrations of *Escherichia coli*.
Figure 15:
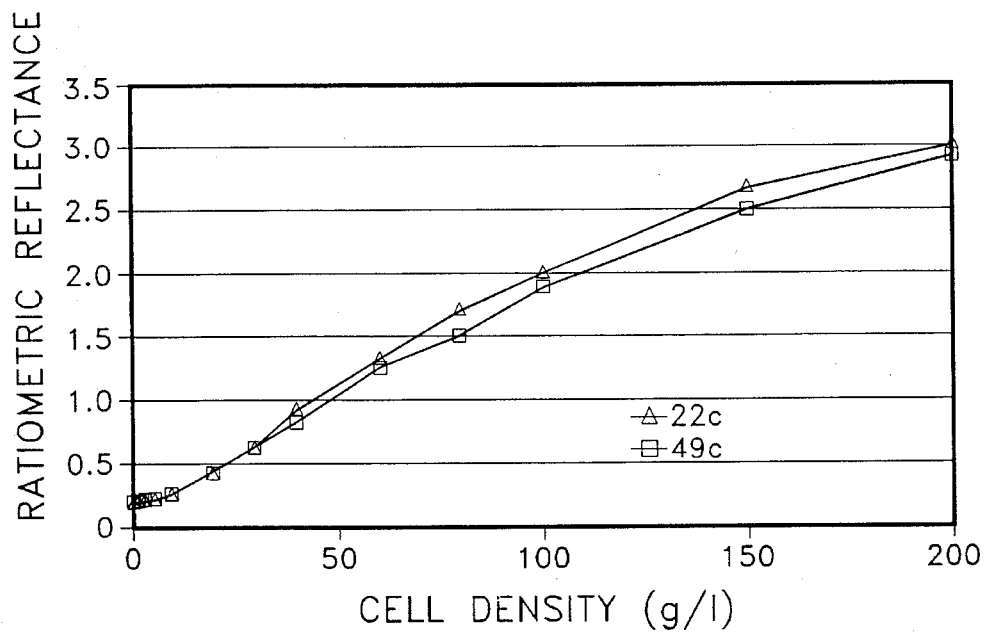
FIG. 15 is a graphic illustration showing ratiometric reflectance as measured by an instrument of the present invention in samples containing varied concentrations of *Saccharomyces cerevisiae* at 22° C. and 49° C.

The effect of the data filtering by the circuitry of the instrument 10 is shown in the comparative raw data signals shown in FIG. 13. As shown in FIG. 13, the filtered raw data (top signal), offset for clarity, is clearly subject to less noise than the unfiltered raw data (bottom signal).

In some embodiments of the invention, two (2) radiation sources are employed such that one (1) of the radiation sources 15' may be utilized for measuring and the other radiation source 15" may be used as a reference radiation source. While variations in temperature and agitation rate affect the absolute reflectance, such variations in temperature and agitation have relatively the same effect on reflectance of both the measuring and reference radiation sources 15', 15", independent of the amount of solids suspended in the liquid medium (e.g., the cell density). Thus, the reflectance of the radiation sources when taken as a ratio of the measuring radiation source 15' to that of the reference radiation source 15" will cancel any effect of temperature and agitation rate variations on the reflectance measurements made by the instrument 10.

FIG. 10 shows the ratiometric reflectance measured by an instrument 10 of the present invention having a first measuring radiation source 15' and a second reference radiation source 15". As shown, the measured ratiometric reflectance of cell density within a *Saccharomyces cerevisiae* culture at 22° C. and 49° C. were not significantly different.

Figure 12:
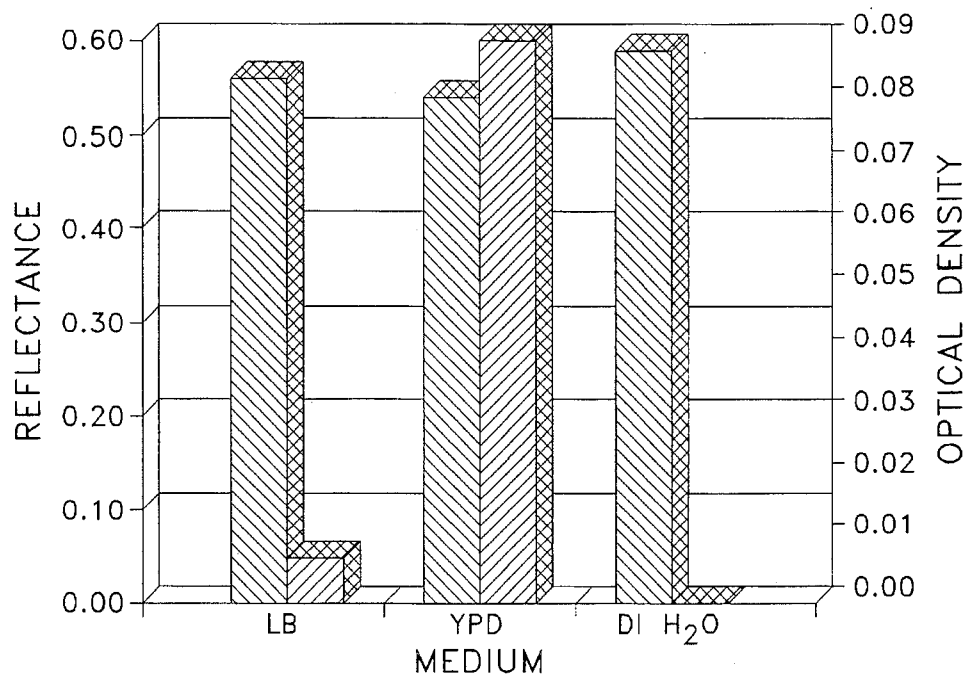
FIG. 12 is a bar graph showing differences in optical properties obtained by reflectance and optical density, in two (2) different biological culture media, as compared to distilled water.

Reflectance measured by the instrument 10 of the present invention is subject to significantly less variation due to coloration of the liquid medium than are optical density measurements of the prior art. This is shown in the bar graph of FIG. 12. Because reflectance measurements are less sensitive to changes in color than optical density measurements, reflectance measurements offer advantages in measuring cell density within cultures where the overall color of the medium, and the resultant optical absorbance of the medium, are high or change during the cultivation of the microorganisms.

The best mode of practicing the present invention as it relates to measurement of culture cell density involves the introduction of the sensing device adjacent to or as part of the culture vessel 22 and 22b of FIGS. 1 & 5. The introduction may be accomplished internally (FIG. 5) or externally (FIG. 1). Radiation resulting from short pulses of light from the radiation source(s) and the detection of reflected radiation will determine the cell density of the culture liquid by continuously measuring the reflectance of the liquid without requiring the constant attendance of a technician. The device may also be directly introduced into a river, lake, water storage vessel or such when it is desired to know the reflectance of the liquid therein. This configuration can be adapted to measure the cell density of drawn samples or within a bypass loop.

The foregoing description of the specific embodiment(s) will fully reveal the general nature of the invention, and certain specific embodiments thereof. The hereindescribed embodiments may be readily modified and/or adapted for various applications without departing from the generic concept, of the invention. Accordingly, it is intended that all such adaptations and modifications be comprehended within the meaning and range of equivalents of the herein-disclosed embodiment(s). It is to be understood that the phraseology or terminology employed herein is for the purpose of description and not of limitation.

What is claimed is:

1. A reflectometric method for measuring the cell density of a culture of microorganisms in a liquid medium so as to facilitate adjustment of process variables which affect cell density, said method comprising the steps of:
   a) providing a reflectometric measuring device having at least one radiation source and at least one radiation sensor, and wherein one of said radiation source and radiation sensor is singular in number;
   b) positioning said device such that said at least one radiation source will cast radiation into said culture and said at least one radiation sensor will receive and sense reflected radiation which has emanated from said at least one radiation source and which has been reflected from said culture;
   c) determining the reflectivity of said culture on the basis of the relative amount of reflected radiation sensed by said at least one radiation sensor;
   d) corresponding the reflectivity of said culture to a current cell density measurement and determining whether said current cell density measurement is within a predetermined range; and,
   e) if said current cell density measurement is outside of said predetermined range, adjusting at least one process variable as necessary to cause said cell density to move into said predetermined range.

2. The method of claim 1 wherein the performance of step (d) comprises:
   establishing a calibration whereby various densities of microorganisms within said liquid culture medium are related to corresponding amounts of reflected radiation sensed by said sensor; and
   utilizing said calibration to arrive at a determination of the present density of microorganisms within said liquid medium.

3. The reflectometric method of claim 1 wherein the reflectometric measuring device provided in step (a) has a single radiation sensor and a plurality of radiation sources.

4. The method of claim 1 wherein steps (a.) and (b.) further comprise:
   positioning said at least one radiation source and said at least one radiation sensor adjacent a window formed in a liquid culture medium vessel wherein said sample is contained.

5. The method of claim 1 wherein steps (a.) and (b.) are accomplished by submersing said at least one radiation source and said at least one radiation sensor within said liquid culture medium.

6. The method of claim 1 wherein step (c.) comprises developing an electrical output from said at least one radiation sensor such that said electrical output will vary relative to the amount of radiation being sensed by said sensor.

7. The method of claim 1 wherein step (a.) further comprises:
   positioning at least one radiation source operative to emit light energy having a wavelength in the range of 300 nm–1050 nm such that the energy emitted by said radiation source will be cast into said liquid culture medium.

8. The method of claim 1 wherein the reflectometric measuring device provided in step (a) has a single radiation source and a plurality of radiation sensors.

9. A reflectometric device for measuring cell density of a culture of microorganisms in a liquid medium, said device comprising:

a housing;

at least one radiation source and at least one radiation sensor positioned within said housing so as to emit and receive radiation outside of the housing, one of said radiation source and radiation sensor being singular in number;

said device being positionable next to the culture of microorganisms such that said at least one radiation source will cast radiation into said culture, and said at least one radiation sensor will receive and sense radiation which has emanated from said at least one radiation source and which has been reflected from said culture;

a computing apparatus for computing the reflectivity of the culture based on the amount of reflective radiation received and sensed by said at least one radiation sensor; and, means for correlating the determined reflectivity of the culture to a cell density measurement value.

10. The device of claim 9 wherein said device incorporates a single radiation sensor and a plurality of radiation sources.

11. The device of claim 9 wherein said housing is submersible within the liquid culture medium.

12. The device of claim 9 wherein said device incorporates a single radiation source and a plurality of radiation sensors.

13. A reflectometric method for measuring the presence of non-liquid inclusions within a liquid medium, said method comprising the steps of:

a) providing a reflectometric measuring device having at least one radiation source and at least one radiation sensor, and wherein one of said radiation source and radiation source and radiation sensor is singular in number;

b) positioning said device such that said at least one radiation source will cast radiation into said liquid medium and said at least one radiation sensor will receive and sense reflected radiation which has emanated from said at least one radiation source and which has been reflected from non-liquid inclusions within said liquid medium;

c) determining a reflectivity value on the basis of the relative amounts of reflected radiation sensed by said at least one radiation sensor; and d) corresponding the determined reflectivity value to a reflectivity value known to be indicative of the presence of non-liquid inclusions within said liquid medium to determine whether, in fact, said non-liquid inclusions are present in said liquid medium.

14. The reflectometric method of claim 13 wherein said non-liquid inclusions are microbial organisms, and wherein the radiation cast in step (b) is of a type suitable for determining the presence of microbial organisms within said liquid medium.

15. The reflectometric method of claim 13 wherein the reflectometric measuring device provided in step (a) has a single radiation source and a plurality of radiation sensors.

16. The reflectometric method of claim 13 wherein the reflectometric measuring device provided in step (a) has a single radiation sensor and a plurality of radiation sources.

17. The reflectometric method of claim 13 wherein step (b) further comprises:

corresponding the measured reflectivity value to a value known to be indicative of a predetermined density of non-liquid inclusions within said liquid medium to thereby arrive at a determination of the present density of non-liquid inclusions within said liquid medium.

18. The reflectometric method of claim 13 wherein said non-liquid inclusions constitute gas bubbles, and wherein the radiation cast in step (b) is of a type suitable for determining the presence of gas bubbles within said liquid medium.

19. The reflectometric method of claim 13 wherein said non-liquid inclusions are solid particles, and wherein the radiation cast in step (b) is of a type suitable for determining the presence of solid particles within said liquid medium.

20. A reflectometric device for measuring the presence of non-liquid inclusions in a liquid medium, said device comprising:

a housing;

at least one radiation source and at least one radiation sensor positioned within said housing so as to emit and receive radiation outside of the housing, one of said radiation source and radiation sensor being singular in number;

said device being positionable next to said liquid medium such that said at least one radiation source will pass radiation into said liquid medium, and said at least one radiation sensor will receive and sense radiation which has emanated from said liquid medium and which has been reflected from said non-liquid inclusions therein;

a computing apparatus for computing a reflectivity value based on the amount of reflective radiation received and sensed by said at least one radiation sensor; and, means for correlating the determined reflectivity value to the presence of non-liquid inclusions in said liquid medium.

21. The device of claim 20 wherein said device is adapted to determine the presence of microbial organisms within a liquid medium, and wherein:

said at least one radiation source and said at least one radiation sensor are adapted to emit and receive radiation of a type which reflects from microbial organisms within said liquid medium.

22. The device of claim 20 wherein said housing is submersible within said liquid medium.

23. The device of claim 20 wherein said device incorporates a single radiation source and a plurality of radiation sensors.

24. The device of claim 20 wherein said device incorporates a single radiation sensor and a plurality of radiation sources.

25. The device of claim 20 wherein said means for correlating the determined reflectivity value to the presence of non-liquid inclusion within said liquid medium further comprises:

means for correlating the determined reflectivity value to a reflectivity value known to be indicative of a predetermined density of non-liquid inclusions within said liquid medium to thereby arrive at a determination of the present density of non-liquid inclusions within said liquid medium.

26. The device of claim 20 wherein said device is a device for determining the presence of gas bubbles within said liquid medium, and wherein:

said at least one radiation source and said at least one radiation sensor are adapted to emit and receive radiation of a type which reflects from gas bubbles within said liquid medium.

27. The device of claim 20 wherein said device is adapted to determine the presence of solid particles within said liquid medium, and wherein:

said at least one radiation source and said at least one radiation sensor are adapted to emit and receive radiation of a type which reflects from solid particles within said liquid medium.

* * * * *